United States Patent [19]
Welt et al.

[11] Patent Number: 5,984,935
[45] Date of Patent: Nov. 16, 1999

[54] TONGUE CLEANER

[76] Inventors: Teodor Welt, Haneviim Str. 54/1; Jonathan Henry Weisberg, Tchernichovsky Str. 4/22, both of Jerusalem, Israel; Radu Budei, Sas. Voinesti Nr. 30, Iassi, Romania, 6600; Codrina Laura Budei, Sas. Voinesti Nr. 30, Iassi, Romania, 6600; Brindusa Cristina Budei, Sas. Voinesti Nr. 30, Iassi, Romania, 6600

[21] Appl. No.: 09/179,823

[22] Filed: Oct. 28, 1998

Related U.S. Application Data

[60] Provisional application No. 60/092,355, Jul. 10, 1998.

[51] Int. Cl.⁶ .............................. A61B 17/24; A61F 9/00; A61F 11/00
[52] U.S. Cl. ............................................ 606/161
[58] Field of Search ...................... 606/161, 162

[56] References Cited

U.S. PATENT DOCUMENTS

| | | | |
|---|---|---|---|
| 2,218,072 | 10/1940 | Runnels | 606/161 |
| 2,583,750 | 1/1952 | Runnels. | |
| 3,890,964 | 6/1975 | Castanedo | 606/161 |
| 4,488,328 | 12/1984 | Hyman. | |
| 4,610,043 | 9/1986 | Vezjak. | |
| 5,282,814 | 2/1994 | Srivastava. | |
| 5,827,308 | 10/1998 | Thakur et al. | 606/161 |

FOREIGN PATENT DOCUMENTS

| | | |
|---|---|---|
| 5031129 | 2/1993 | Japan. |
| 9051898 | 2/1997 | Japan. |
| 9294688 | 11/1997 | Japan. |

*Primary Examiner*—Michael Buiz
*Assistant Examiner*—Vy Q. Bui
*Attorney, Agent, or Firm*—Jacobson, Price, Holman & Stern, PLLC

[57] ABSTRACT

The invention provides a tongue scraping and cleaning device, including a head configured to be comfortably moved along the top surface of a tongue inside and outside of a mouth, the head including a base portion having an upper face and a lower face and a plurality of spaced-apart blades formed with active scraping surfaces and at least partly projecting from the upper face so as to cause the material scraped off the tongue to be trapped between the blades, and means for grasping the head and imparting controlled scraping movements along the tongue to effect its cleansing.

14 Claims, 7 Drawing Sheets

TONGUE CLEANER

This application is based upon U.S. Provisional Application No. 60/092,355, filed Jul. 10, 1998.

FIELD OF THE INVENTION

The present invention relates to a tongue scraping and cleaning device.

BACKGROUND OF THE INVENTION

Tongue cleaning instruments of various kinds are per se known. For example, U.S. Design Pat. Nos. 367,707 and 377,417 describe manually operated razor blade-type tongue scrapers; U.S. Design Pat. Nos. 301,372 and 4,488,328 disclose loop-type tongue scrapers. Other kinds, such as brush-type instruments and combined toothbrush and tongue scrapers, are also known.

The main disadvantages of the above-mentioned and other kinds of tongue scraping instruments reside in the fact that due to their basic inappropriate construction, these instruments do not satisfactorily fulfill their task. The known manually operated razor blade-type scrapers, having a larger dimension perpendicular to the direction of movement along the tongue, do not properly clean the side surface portions of the tongue, nor are they fit to clean the back portion of the tongue, at least without the danger of wounding the delicate tissues inside the mouth. Another shortcoming of these prior art instruments resides in the fact that the scraped-off, bacteria-containing material spreads throughout the oral cavity and is thus not properly removed.

It is therefore a broad object of the present invention to provide a tongue scraping and cleaning device having an optimized ergonomic structure.

It is a further object of the present invention to provide a tongue scraping and cleaning device having improved scraping and cleaning capability and efficiency.

SUMMARY OF THE INVENTION

In accordance with the present invention, there is therefore provided a tongue scraping and cleaning device comprising a head configured to be comfortably moved along the top surface of a tongue inside and outside of a mouth, said head including a base portion having an upper face and a lower face and a plurality of spaced-apart blades formed with active scraping surfaces and at least partly projecting from said upper face so as to cause the material scraped off the tongue to be trapped between said blades, and means for grasping said head and imparting controlled scraping movements along the tongue to effect its cleansing.

BRIEF DESCRIPTION OF THE DRAWINGS

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DETAILED DESCRIPTION OF PREFERRED EMBODIMENTS

Figures 1, 2, 3:
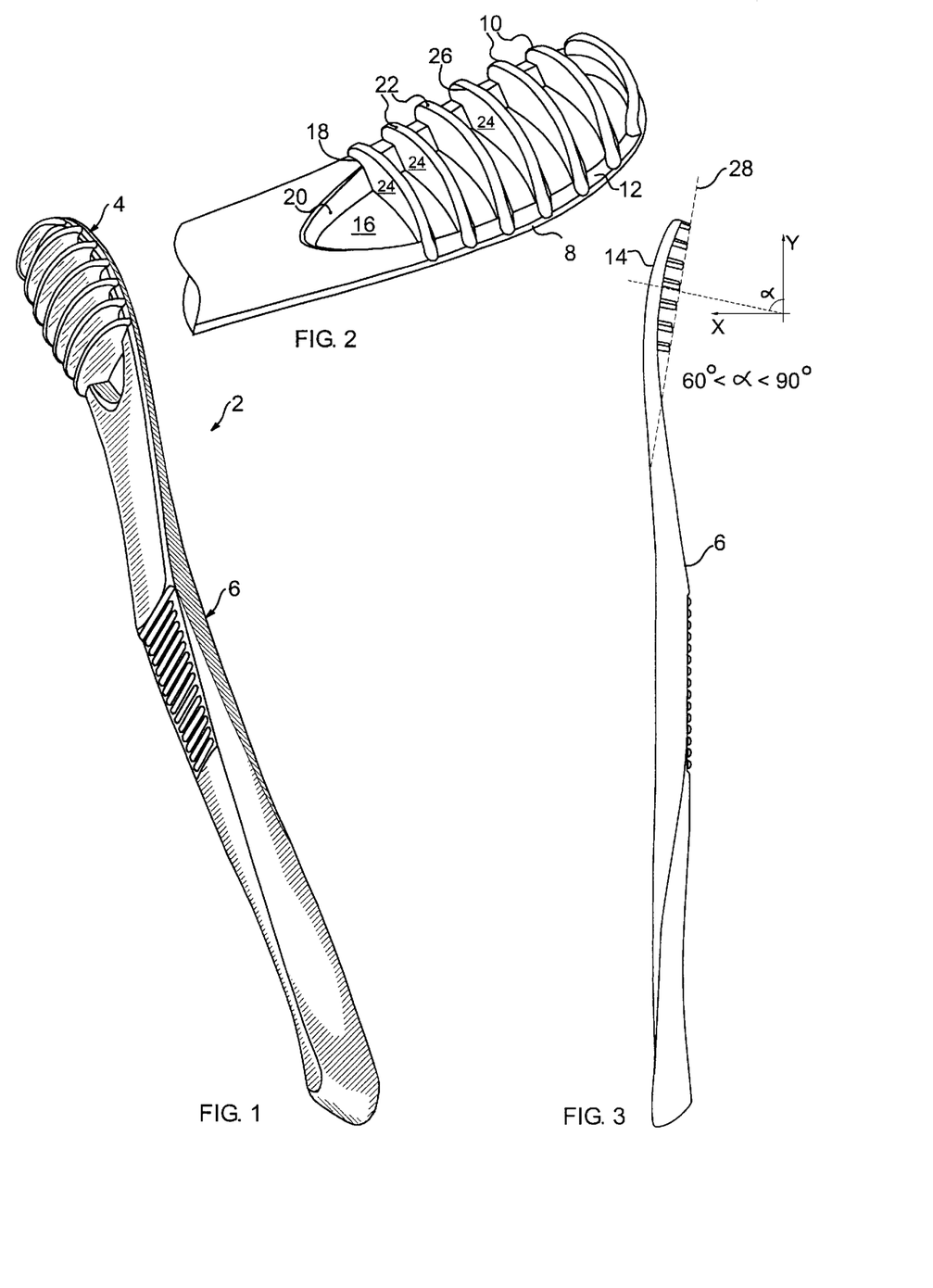
FIG. 1 is a perspective view of a preferred embodiment of a tongue scraper according to the present invention.
FIG. 2 is an enlarged, perspective view of the head portion of the device of FIG. 1.
FIG. 3 is a side view of the device of FIG. 1.

Referring now to the drawings, there is illustrated in FIGS. 1 to 3 a preferred embodiment of the tongue scraping and cleaning device 2 according to the present invention. The device 2 is essentially constituted by two portions: a head 4 and grasping means 6, which may be made of any suitable material such as plastic, as an integral unit or as two separate, detachably interconnectable units, rendering the head disposable after one or more uses.

The sole purpose of the grasping means is to hold and manually move the head along the top surface of a tongue, in a straight and/or circular motion, while applying controlled pressure. Hence, while the most commonly used grasping means is embodied by a handle of any kind, including those of the type employed with a toothbrush, other types of handles or grasping means could just as well be used. For example, instead of a handle, the head 4 may be provided with knurled side recesses (not shown), so that it may be gripped by two fingers, or with a loop or other such means for engaging one finger, to effect the reciprocating movements of the device along a surface of a tongue.

The head 4 comprises a base 8 and a plurality of spaced-apart blades 10, e.g., between 4 and 9 blades. The base 8, having an upper face 12 and a lower face 14, may be embodied as a solid, relatively thin plate, or, as shown in FIG. 2, only as a frame defining an opening 16. The blades 10 may be formed integrally with, or mounted on, the base 8. In the preferred embodiment shown, the blades 10 are slightly curved or concave and are made with a shoulder 18 at each of their sides to facilitate attachment to the upper face 12 and the inner peripheral face 20 of frame-like base 8. Naturally, base 8 may be formed with suitable shallow slots for accommodating the edges of the blades along shoulders 18. Alternatively, edges of the blades may be slightly embedded in the base, irrespective of its shape.

The combined base 8 and blades 10 forming head 4 are rendered an ergonomic configuration, preferably an elliptical shape without sharp corners around the outside surfaces. On the other hand, each of the blades 10 has an active surface 22 which is advantageously non-rounded and forms, along with the leading side wall 24, a relatively sharp edge constituting an effective scraping edge 26, which may be straight or curved. Furthermore, the blades 10 are advantageously not mounted perpendicular to the base 8, but rather at a slight inclination thereto, as shown in FIG. 3. The angle of inclination $\alpha$ should preferably be $60°<\alpha<90°$. While the lower face 14 of base 8 is rounded or convex, blades 10 are each made of a height so that the active surfaces 22 will lie within common plane 28.

The number of blades 10, the spacing between the blades and their height are so chosen that the scraped-off material will be accumulated and retained therebetween, as opposed to the known scrapers whose sole task is merely to scrape the material off the tongue. The accumulated material can then be washed off, or the device may be altogether discarded. Openings between blades 10, constituting portions of opening 16 formed in the base, serve a non-essential, but important, role for the purpose of washing or otherwise removing the accumulated scraped-off material from the device.

Optionally, there may be added an antiseptic coating or antiseptic-laden strips secured on the side adjacent to the scraping edge, or both sides, of each of the blades, in order to provide an antiseptic substance to medicate the scraped area of the top surface of the tongue.

Figure 4:
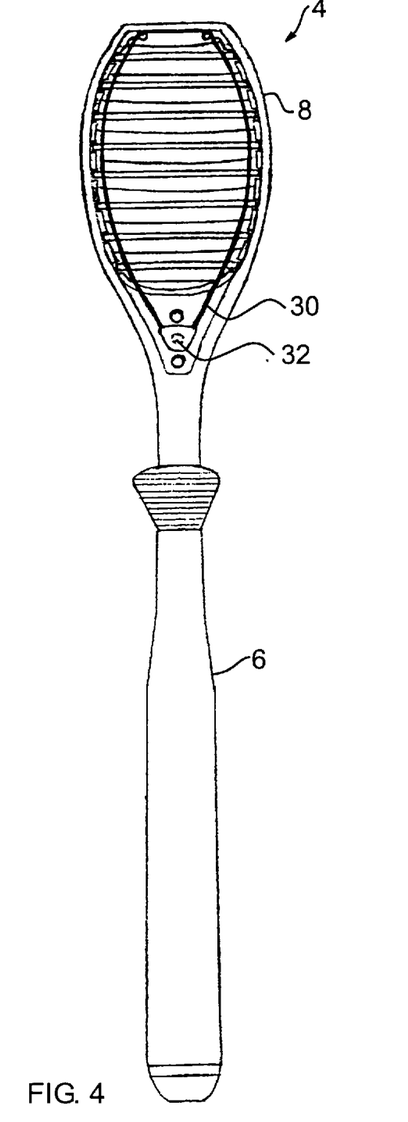
FIGS. 4 and 5 are respectively top and side views of a further embodiment of the device according to the present invention.
Figure 5:
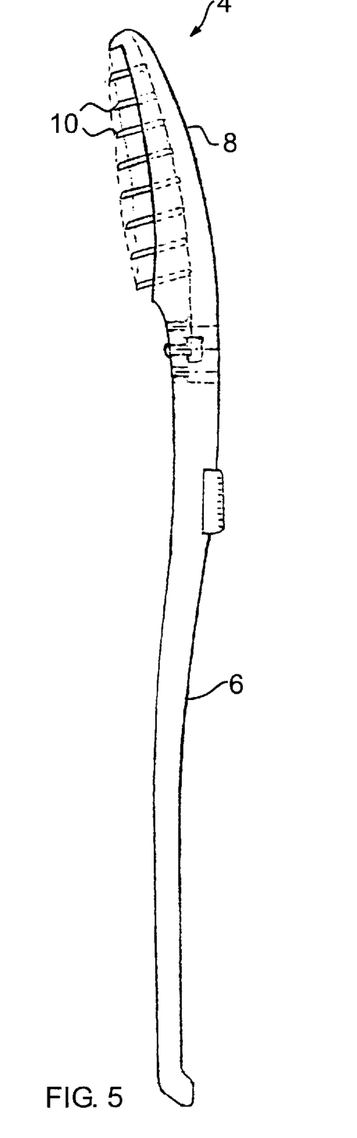

Referring to FIGS. 4 and 5, there is illustrated another embodiment of construction of the head of device 2. The blades 10 are resiliently affixed to base 8 so as to impart to each blade 10 the capability to individually move in a direction traversing the plane of the base, thereby being more adjustable to the contours of the tongue. There is therefore provided a rubber band 30 surrounding the inner periphery of the frame-like base, which rubber band can be tensioned to a desired degree by means of an adjustable tensioning pulley 32. The blades 10 are held at their lateral sides inside grooves formed in the walls of the base. Instead of the rubber band, each blade may be mounted on a spring element.

Figure 6:
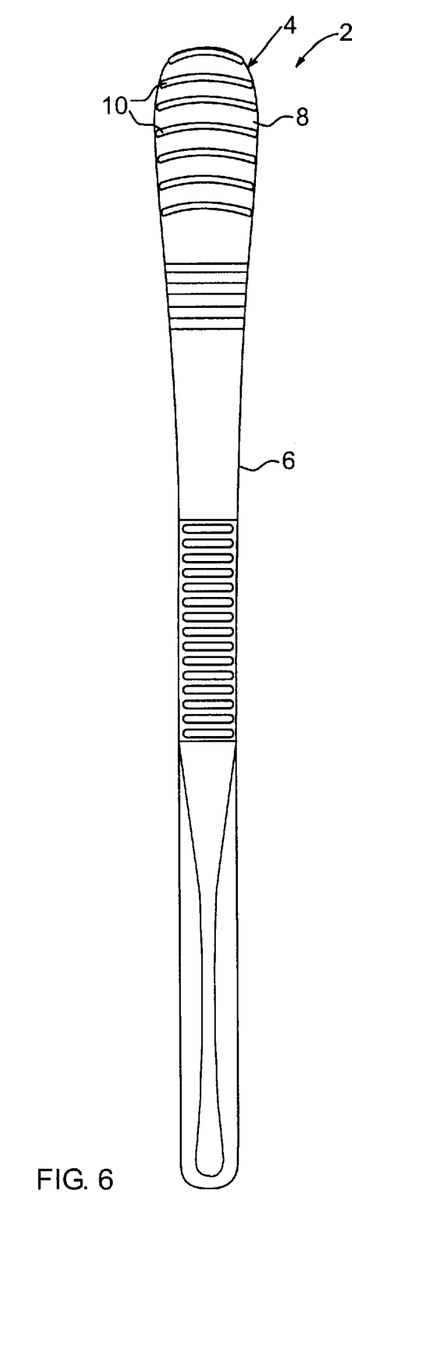
FIGS. 6 and 7 are respectively top and side views of a still further embodiment of the invention.
Figure 7:
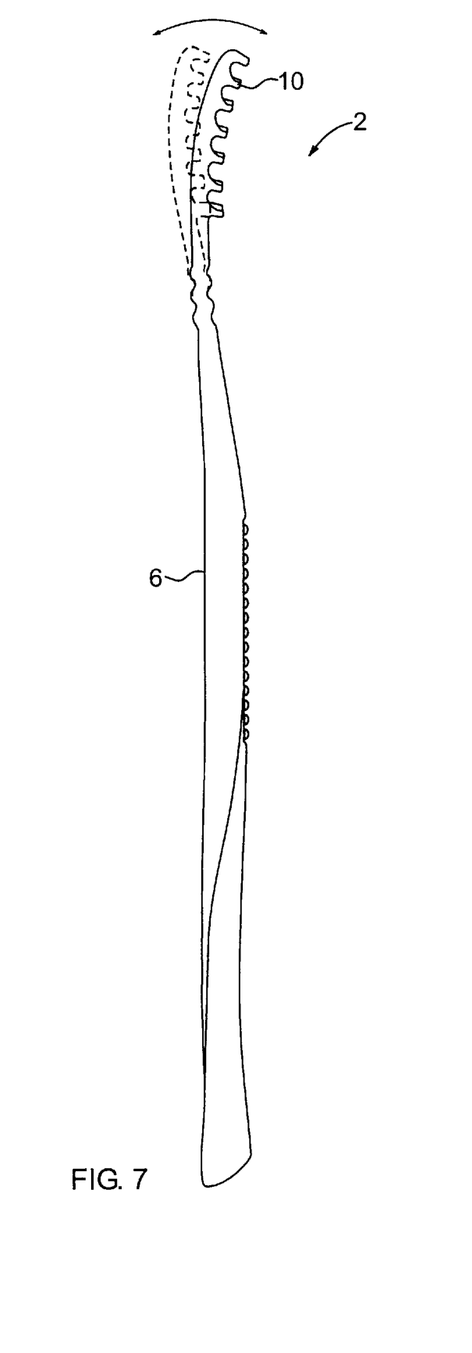

FIGS. 6 and 7 illustrate a device 2 according to the present invention, in which the base 8 of head 4 is solid and the grasping means 6 is flexibly articulated to head 4, as indicated by the hatched lines in FIG. 7. This flexibility facilitates the application of a controlled pressure of the scraping head on the surface of the tongue.

Figure 8:
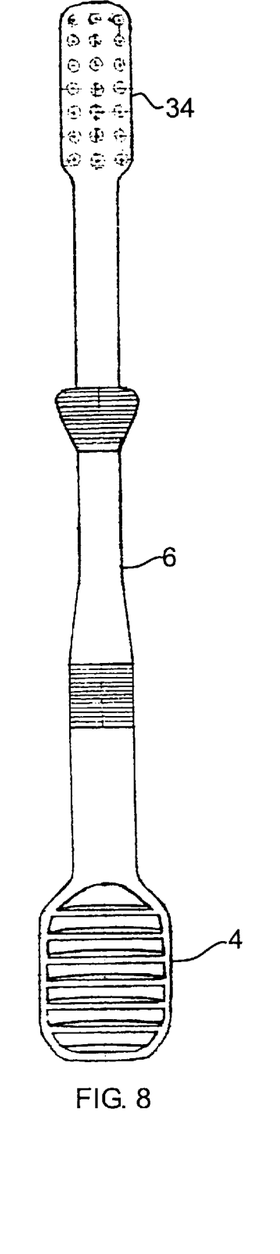
FIGS. 8 and 9 are respectively top and side views of a combined tongue scraping device and toothbrush.
Figure 9:
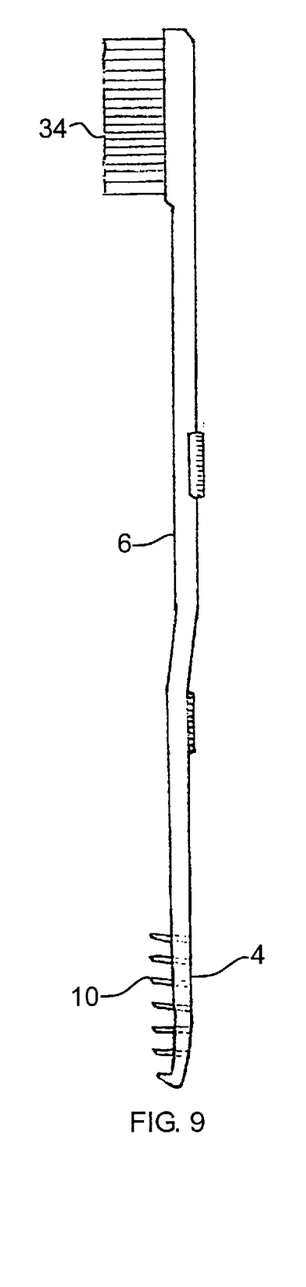

A combined tongue scraping head and toothbrush is shown in FIGS. 8 and 9. The scraping head 4 and the toothbrush 34 share a common gripping means 6, made in the form of a handle.

Figure 10:
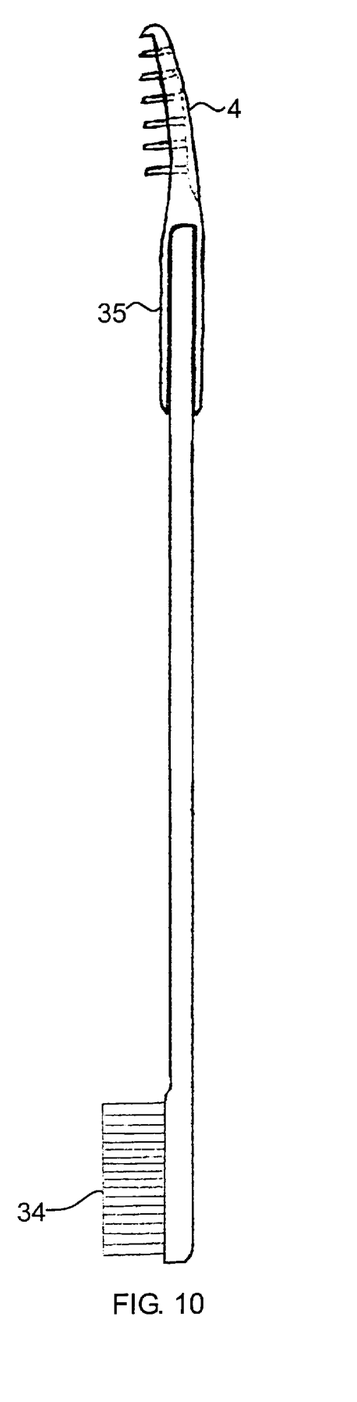
FIG. 10 is a side view of a device according to the present invention having a detachable scraping head.

FIG. 10 illustrates a scraping head 4 according to the present invention, having connecting means 35 for facilitating a detachable connection between scraping head 4 and the non-active end of a toothbrush.

Figure 11:
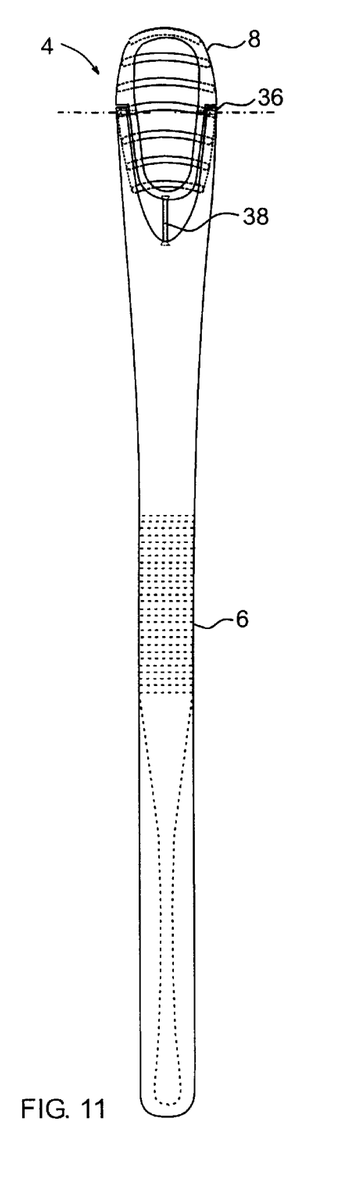
FIG. 11 is a front view of a device according to the present invention having a movable head.
Figures 12, 13:
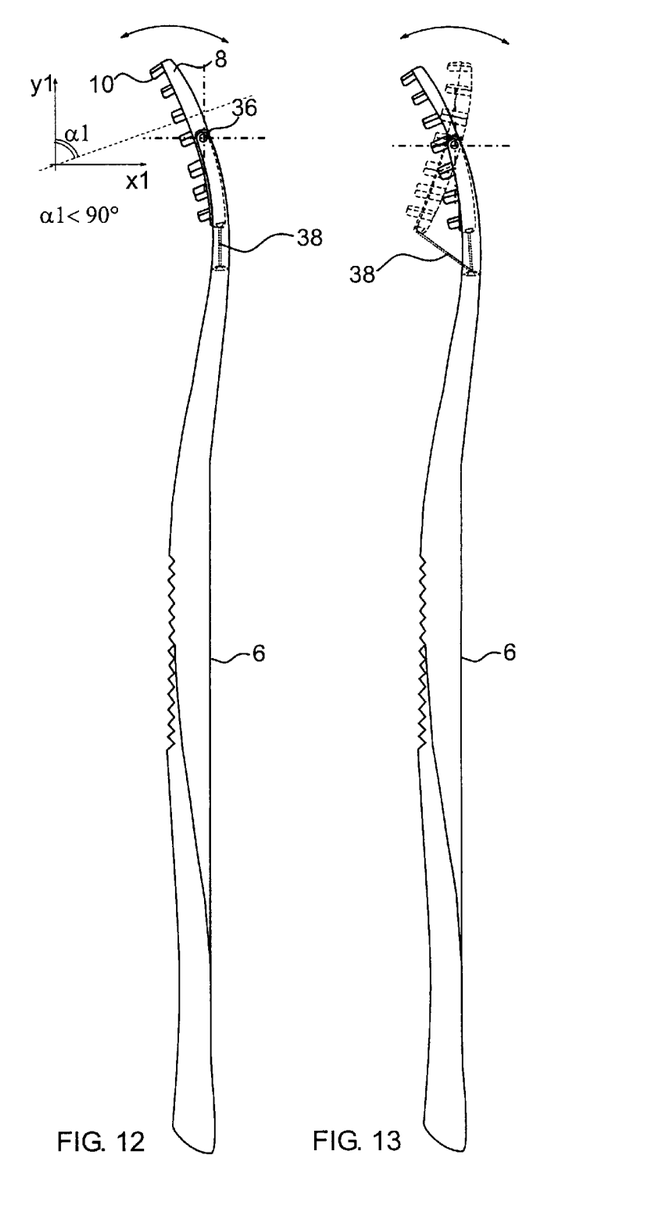
FIGS. 12 and 13 are side views of the device of FIG. 11, showing the head in two operating positions.

Referring now to FIGS. 11 to 13, there is illustrated another embodiment of a device 2 having a movable head. The head 4 is pivotably articulated to the split-arms grasping means 6 by means of axles or pins 36. In order to ensure a proper controlled swinging movement about pins 36, a spring element 38 is provided, interconnecting the base 8 with grasping means 6. Depending upon the angle applied by the user on the head against the surface of the tongue, the head will assume various angles with respect to the handle. At the end of the scraping operation, the head will return to its closed state, as shown in FIG. 12.

Figure 14:
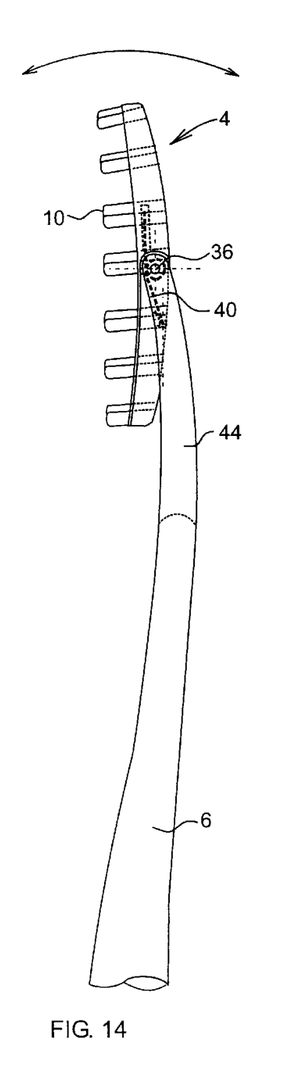
FIG. 14 is a side view of a modification of the device of FIG. 12.

Turning to FIG. 14, there is illustrated a modification of the device of FIGS. 11 to 13, in which, instead of the exteriorly disposed spring element 38, there is provided a concealed biasing spring 40, e.g., a leaf spring, wound around the pins 36.

Figure 15:
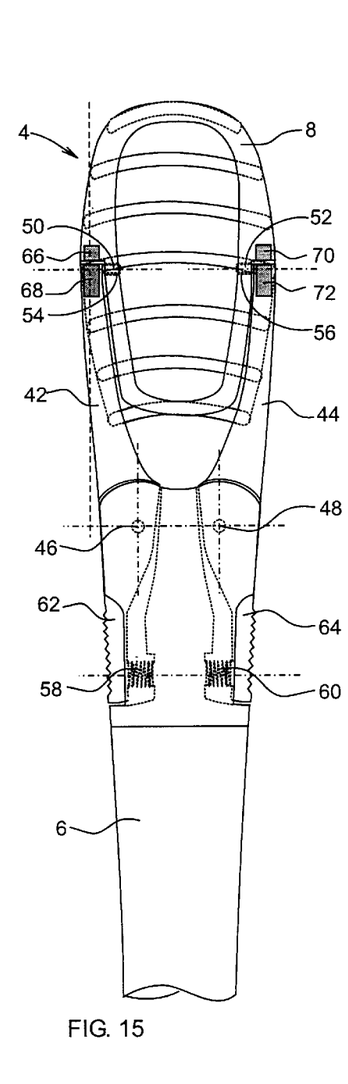
FIGS. 15 and 16 are front and side views of a still further embodiment of a device according to the present invention having a detachable head.
Figure 16:
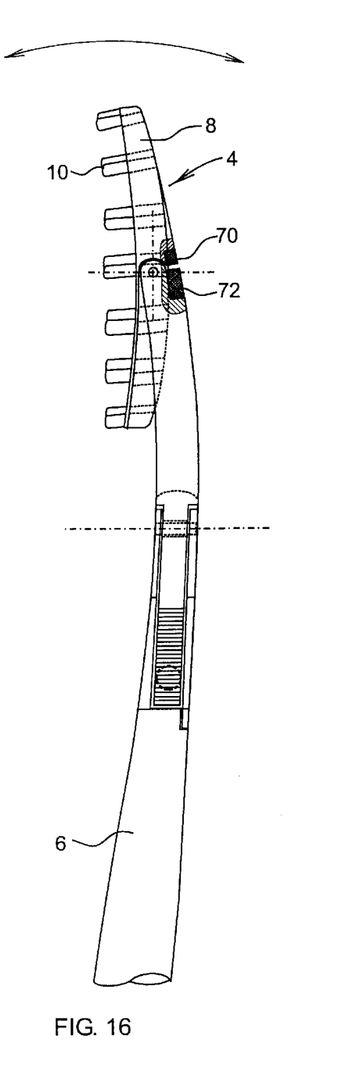

Another type of device having a disposable head is illustrated in FIGS. 15 and 16. The base 8, bearing the blades, can be disconnected from arms 42, 44 for replacement. The arms 42, 44 are pivotably mounted about axes 46, 48 on the grasping means 6, and are provided with pins 50, 52, loosely engaging bores 54, 56 made at the lateral sides of head 4. The pivoting arms 42, 44 are suitably biased by means of springs 58, 60 so as to maintain the pins 50, 52 within the bores 54, 56. Upon depressing the knobs 62, 64 against the force of the springs, the pins 50, 52 disengage from the bores, thus freeing head 4 from the handle for replacement. A pair of magnets 66, 68; 70, 72 is also provided on each lateral side of the device adjacent to the pivot pins 50, 52. Each magnet in a pair is magnetized in an opposite polarity so as to limit the movement of the head 4 about the pivot pins 50, 52 during use, similar to the effect of the biasing spring 40 of FIG. 14.

Figure 17:
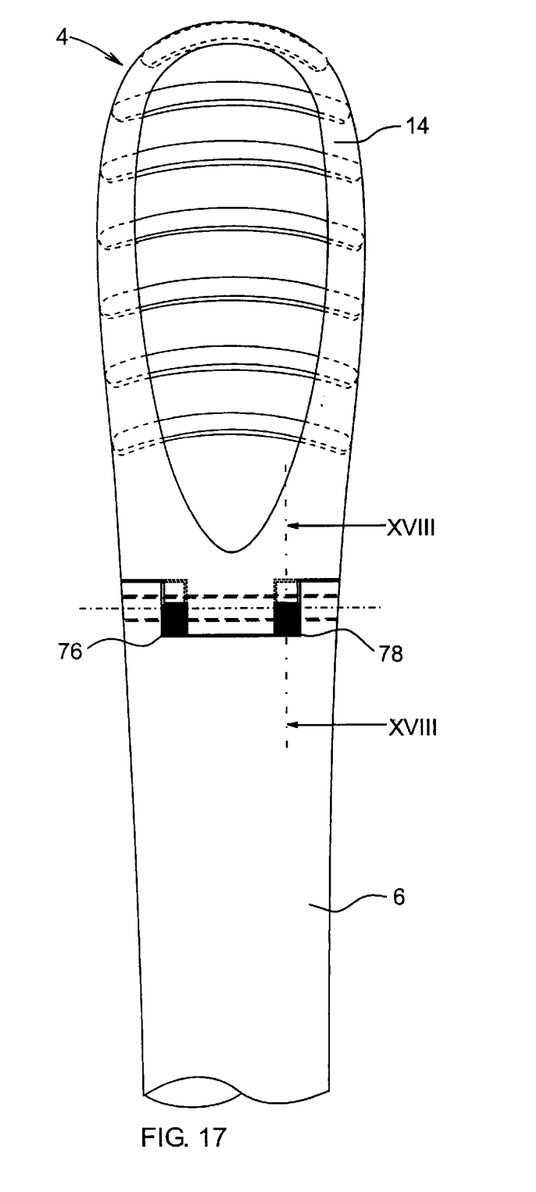
FIG. 17 is a front view of another further embodiment of the device.
Figure 18:
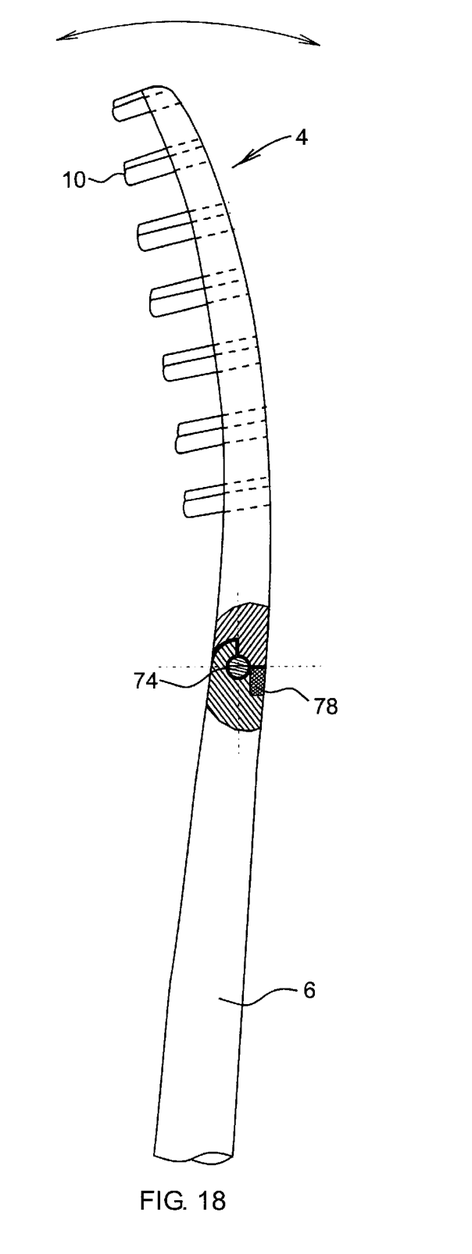
FIG. 18 is a side view, partly in cross-section along lines XVIII—XVIII, of the device of FIG. 17.

FIGS. 17 and 18 illustrate another embodiment of the device in which the head 4 is articulated to the grasping means 6 by a pivot 74 engaging and linking suitably configured end portions thereof. In order to furnish the head 4 with a resilient quality with respect to the grasping means 6, especially for absorbing any over-pressure exerted by the user during use, there are provided elastic members 76, 78, i.e., small rubber cushions, rendering the head 4 flexible with respect to the grasping means.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A tongue scraping and cleaning device, comprising:
   a head configured to be comfortably moved along the top surface of a tongue inside and outside of a mouth, said head including a base portion constituted by a frame defining a substantially oval opening and having an upper face and a lower face and a plurality of spaced-apart curved blades formed with active scraping surfaces and at least partly projecting from said upper face so as to cause the material scraped off the tongue to be trapped between said blades, to be eventually washed off and removed through said opening, and
   means for grasping said head and imparting controlled scraping movements along the tongue to effect its cleansing.

2. The device as claimed in claim 1, wherein said base is generally elliptically shaped.

3. The device as claimed in claim 1, wherein said blades are substantially flat.

4. The device as claimed in claim 1, wherein said blades are curved.

5. The device as claimed in claim 1, wherein at least the upper face of said base is concave.

6. The device as claimed in claim 1, wherein said blades have an active scraping surface formed with a non-rounded leading edge.

7. The device as claimed in claim 1, wherein the active scraping surfaces of said blades define a plane.

8. The device as claimed in claim 1, wherein the active scraping surfaces of said blades define a curved surface.

9. The device as claimed in claim 1, wherein said blades are inclined with respect to the plane of the portion of the base from which they project.

10. The device as claimed in claim 1, wherein at least some of said blades are resiliently mounted at least indirectly on said base.

11. The device as claimed in claim 1, wherein said grasping means is a handle connected to, or made integral with, said head.

12. The device as claimed in claim 11, wherein said head is detachably connected to said handle.

13. The device as claimed in claim 11, wherein said head is resiliently attached to said handle.

14. The device as claimed in claim 11, wherein said head is pivotably articulated to said handle.

* * * * *